United States Patent
Milánkovits

(10) Patent No.: US 6,432,935 B1
(45) Date of Patent: Aug. 13, 2002

(54) PHARMACEUTICAL COMPOSITIONS, MAINLY VAGINAL SUPPOSITORY, CONTAINING MANY DIFFERENT ACTIVE INGREDIENTS

(76) Inventor: Márton Milánkovits, Meredek u. 52., H-1112 Budapest (HU)

( * ) Notice: Subject to any disclaimer, the term of this patent is extended or adjusted under 35 U.S.C. 154(b) by 0 days.

(21) Appl. No.: 08/776,273

(22) PCT Filed: Jul. 20, 1995

(86) PCT No.: PCT/HU95/00036

§ 371 (c)(1),
(2), (4) Date: Jan. 22, 1997

(87) PCT Pub. No.: WO96/03135

PCT Pub. Date: Feb. 8, 1996

(30) Foreign Application Priority Data

Jul. 25, 1994 (HU) ............................................. 9402182
Oct. 10, 1994 (HU) ............................................. 9402182

(51) Int. Cl.⁷ ...................... A61K 31/65; A61K 31/655; A61K 31/70; A61K 31/23
(52) U.S. Cl. ........................ 514/157; 514/154; 514/386; 514/29; 514/31; 514/967; 514/552; 514/396; 514/966
(58) Field of Search ................................ 514/396, 966, 514/157, 386, 29, 31, 154, 967, 552

(56) References Cited

U.S. PATENT DOCUMENTS 4,698,359 A * 10/1987 Niederer et al. ............. 514/396
5,096,889 A 3/1992 Hector et al. ................. 514/43

FOREIGN PATENT DOCUMENTS

| EP | 0 125 759 | 3/1984 |
| EP | 0 241 175 | 3/1987 |
| EP | 0 432 638 | 12/1990 |
| GB | 2 126 086 | 8/1983 |

OTHER PUBLICATIONS

Merck Index, 1977, Entries 6468, 9377, 6079, 6658, 6346, 2412, 16, 3626, 2068.*

Chemical Abstracts AN 1981:30764, Dockner et al (US patent 4,218,460). Aug. 19, 1980.*

CHemical Abstracts AN 1989:121425, Payne et al *DE 3800256). Jul. 21, 1988.*

Chemical Abstracts AN 1993:479972, Tari et al. Jun. 1992.*

Chemical Abstracts AN 1991:499151, Murav'ev et al. Jun. 1990.*

* cited by examiner

Primary Examiner—Theodore J. Criares
Assistant Examiner—Jennifer Kim
(74) Attorney, Agent, or Firm—Haugen Law Firm PLLP

(57) ABSTRACT

Compositions comprising an antibiotic, sulphonamide, at least one an antiquagul agent, e.g., clotrimazol (bis-phenyl-(2-chlorophenyl)-1-imidazolyl-methane), natamycin, or nystatin, and 5-nitro-metronidazol (5-nitro-inidazoles) e.g., (metronidazol or tinidazol or nimorazol) and a pharmaceutically acceptable carrier. The compositions are useful mainly as vaginal suppositories.

6 Claims, No Drawings

PHARMACEUTICAL COMPOSITIONS, MAINLY VAGINAL SUPPOSITORY, CONTAINING MANY DIFFERENT ACTIVE INGREDIENTS

This invention relates to novel pharmaceutical compositions and their uses as suppositories, especially vaginal suppositories, ointments, vaginal drops and talc powders, and painting solutions.

BACKGROUND OF THE INVENTION

A variety of vaginal suppositories are currently commercially available. The attending physician ordinarily decides which composition is best suited to the patient's needs following physical examination.

For treating vaginal mycosis, Canesten (active ingredient is clotrimazol; bis-phenyl-(2-chlorophenyl)-1-(imidazolyl)-methane; and Pimafucin (the active ingredient is natamycin-primaricin) are most commonly used. For fungal and protozoan infection, Klion-D (the active ingredient is metronidazol; 1-(2'-hydroxiethyl)-2-methyl-5-nitroimidazol and myconasol-nitrate) is used. For protozoa infection, Klion vaginal suppository (active ingredient is metronidazol) is commonly used.

Certain compositions exert their effects through the disinfective action of iodine. These include Betadine (iodine is released from the carrier). Other vaginal suppositories feed the natural flora of the vagina. These include Genia-92 nutrients, e.g., folic acid, lactic acid, lactose, and lactamine.

A common disadvantage of the above compositions is that none of them makes possible the combination of (i) bactericide (for aerobic and anaerobic bacteria), involving anti-Mobiluncus and anti-Gardnerella, and (ii) fungicide and (iii) anti-protozoa effect simultaneously. Moreover, they have no antiviral effect.

SUMMARY OF THE INVENTION

The invention relates to compositions which make possible the attack of pathogens, and which simultaneously aid in the body's antiviral struggle. The invention facilitates rapid and simple selection of the safest and most useful compositions.

The basis of the invention is the discovery that a unique combination of active ingredients has numerous advantages over the art. In a preferred embodiment, the invention relates to compositions comprising a) an antibiotic, preferably chloramphenicol or erythromycin; b) sulphonamide, preferably sulphadimidin; c) antifungal component, e.g., at least one of clotrimazol (bis-phenyl-(2-chlorophenyl)-1-imidazolyl-methane), natamycin, or nystatin; and d) 5-nitro-metronidazol i.e., 5-nitro-imidazoles, see Goodman and Gilmann's, *The Pharmacological Basis of Therapeutics*, $9^{th}$ ed., 1996, page 995 (ISBN 0070026266) (metronidazol or tinidazol or nimorazol) and a pharmaceutically acceptable carrier.

It has been found that the effect of the antibiotic or sulphonamide ingredient is unexpectedly intensified by the other active ingredients. This effect is true in both directions; for example the antibacterial (especially the anti-Chlamydia) effect of chloramphenicol and sulphonamide is greatly increased by the present compositions. Additionally, an increased inhibitory effect of chloramphenicol and metronidazol against anaerobe pathogens (e.g., *B. fragilis*) was observed. The antibacterial effect of the sulphonamide and metronidazol antibiotics also unexpectedly potentiated generally against each pathogenic bacterium, in the antifungal protection provided by the fourth component. Thus, the treatment spectrum is broader and the effect of the combination is much stronger than would be expected from its individual components, while simultaneously decreasing the necessary dosages for treatment compared to the individual active ingredients. This results in a decrease of the possible side effects while using the present combination of elements. Another significant advantage of the solution according to the invention is that [the usual] drug resistance does not occur.

DETAILED DESCRIPTION OF THE INVENTION

In a preferred embodiment, the composition comprises a vaginal suppository comprising:

| Component | Amount |
| --- | --- |
| a) Antibiotic | 0.10–0.15 g/dose of preferred antibiotic; |
| b) Sulphonamide | 0.10–0.15 g; |
| c) Clotrimazol, or | 0.090–0.10 g |
|    Natamycin, or | 0.025–0.075 g |
|    Nystatin | 0.1 g |
| d) 5-nitro-metronidazol (5-nitro-imidazoles) | 0.40–0.50 g. |

The pharmaceutical composition having components b, c, and d, can be used even in the case of an allergy.

The preferred carrier for the compositions is polyethylene-glycol, but other suitable carriers may also be employed. The amount of polyethylene-glycol supplements the combination of the active ingredients to the necessary amount in case of a 10-unit package.

With respect to the antibiotic component, oxytetracyclin or erythromycin can be used in the same amounts instead of chloramphenicol. Erythromycin is especially preferred because of its strong antibiotic effects and low allergic effects. Erythromycin's wide range of efficacy makes it effective against *Chlamydia trachomatis* and can be administered during pregnancy. Other antibiotics can also be used mainly, such as those capable of killing *Chlamydia trachomatis*. The necessary amount of these antibiotics is the same percentage of the standard oral doses the in case of the chloramphenicol or oxytetracyclin i.e. any locally applicable antibiotic can be used and $\frac{1}{20}^{th}$ of the daily dosage is necessary. A ±50% or more alteration is possible. The same alterations are acceptable concerning the other components of the invention.

Other sulphonamides can also be used instead of sulfadimidin. Sulfadimidin is a preferred component, but it can be replaced with other active ingredients having a similar structure.

As to component c) of the compositions, clotrimazol and nystatin are most preferred. With respect to component d), metronidazol is most preferred.

The combination of elements used in the vaginal suppositories are more effective and qualitatively different from the separate administration of the individual components. Administration of the present compositions has resulted in complete recovery in cases when recovery could not be reached by the separate administration of the components. The compositions are useful in a variety of applications and treatments, including the following:

Prophylactic Use. Use of the suppository prevents infection from infected swimming-pool water or sexual activity.

The composition is indispensable prior to gynecological operations (especially utero-vaginal interventions) as a prophylactic suppository.

Treatment of infection. For infections, use of the preparation prior to infections results in absolute recovery in 90% of the cases. Since systemic treatment is not needed, a smaller dose is sufficient. Also, because a smaller dose is administered, the risk of possible side effects is minimized. Cessation of treatment results in the side effects disappearing (for local treatments there were no side effects observed). Resistance of the pathogens against the components used is also obviated because in local treatment the relatively small amount of preparation applied absolutely kills the pathogens.

Treatment of Chronic Vaginitis. Presently laser surgery, conventional surgery, cryocoagulation or electro-cauterisation is used for the treatment of the cervicalization, (ectopium) or the slightly positive epithelial differences (such as the slightly acetic acid positive epithelium, or the decrease of the iodine positively), or other kinds of slightly pathological epithelium and $P_3$ cytological findings, respectively.

The suppository of the invention promotes the spontaneous healing of the bleed, inflamed portion of the uterus. As a result, the above-described conventional treatments become unnecessary. Constant inflammation plays a decisive role in the formation of cancer of the cervix of the uterus. Application of the suppository according to the invention greatly diminishes the risk of the formation of the cancer of the cervix of the uterus, by stopping the inflammation. Metronidazole has a certain anticancer effects, which are observed during radiation treatment of tumors, where it increases the efficacy of the radiation treatment.

Following treatment with the suppository, the laboratory findings improved from $P_3$ cytological to $P_2$ or $P_1$, without exception (and the epithelium became normal kolroscopically too).

Antiviral effect. The present combination acts against viral infections, possibly by killing all non-viral pathogens, enhancing the immunocapacity of the body against the viruses.

In those cases when, because of inflammation and vaginal discharge, the treatment of the Condyloma acuminatum (caused by the human papilloma virus) failed, treatment using the present suppository, the local Phodophyllin treatment proved to be permanently successful. Moreover, it was observed that patients with frequently recurring herpes genitalis, became permanently free of symptoms following the treatment with the preparation.

The preparation according to the invention can also be administered to pregnant women (erythromycin is the preferred antibiotic component).

The compositions according to the invention were tested in 300–400 cases, with 300–400 controls. In all cases, the full microbiological examination included Chlamydia trachomatis and the Mycoplasmas.

Preparation of the compositions according to the invention can be carried out by methods known in the art for the preparation of such compositions.

The following examples will serve to further typify the nature of the invention but should not be construed as a limitation on the scope thereof, which is defined solely by the appended claims.

EXAMPLE 1

Vaginal suppositories are made with the following ingredients: Chloramphenicol 0.08 g, Sulfadimidin 0.12 g, Clotrimazol 0.15 g, Metronidazol 0.40 g, Carrier: polyethyleneglycol.

EXAMPLE 2

Vaginal suppositories are made with the following ingredients: Chloramphenicol 0.1 g, Sulfadimidin 0.1 g, Clotrimazol 0.1 g, Metronidazol 0.40 g, Carrier: polyethyleneglycol. Additional carriers such as butyrum cacao can also be used.

The present combination can be used in other applications (other than vaginal suppositories) such as ointments, talc powder, solution, painting solutions, or vaginal drops, etc.

Ointment preparations contain the combination of the active ingredients in the same ratio as in the vaginal suppository, together with an ointment base, with yellow Vaseline and other components known per se, if required. This preparation is especially effective in the treatment of tissue damage (diabetes mellitus, burning, etc). The talc powder preparation contains the active ingredient combination in solid form, with solid carriers such as talc, etc. The painting solutions and vaginal drops are prepared with an appropriate organic solvent. The vaginal drop solutions are useful in pediatric gynecology, but can also be used for adults in adequate doses.

The present compositions can also optionally contain borax ($NA_2B_4O_7 \cdot 4H_2O$).

The pharmaceutical compositions mentioned above can be prepared by known techniques used in the preparation of the pharmaceutical compositions.

What is claimed is:

1. A pharmaceutical composition comprising:

(a) an antibiotic;

(b) sulfadimidin;

(c) nystatin;

(d) metronidazol; and (e) a pharmaceutical carrier, wherein said antibiotic, said sulfadimidin, said nystatin, and said metronidazol are present in synergistic effective amounts.

2. The pharmaceutical composition according to claim 1, further comprising borax.

3. The pharmaceutical composition according to claim 1, wherein said composition is selected from the group consisting of vaginal suppositories, ointments, solutions, painting solutions, vaginal drops and powders.

4. The pharmaceutical composition of claim 1 comprising:

(a) 0.10–0.15 g of said antibiotic, wherein said antibiotic is selected from the group consisting of chloramphenicol, erythromycin and oxytetracyclin;

(b) 0.10–0.15 g of said sulfadimidin;

(c) 0.1 g nystatin; and (d) 0.40 g to about 6.5 g of said metronidazol.

5. The pharmaceutical composition according to claim 1 wherein said nystatin is effective against a Candida species.

6. The pharmaceutical composition according to claim 1 wherein said antibiotic is selected from the group consisting of chloramphenicol, erythromycin, oxytetracyclin, ampicillin, cyprofloxacin, neomycin, polymixin, unasyn, augmentin, oxycillin, cefaclor, gentamicin, clarithromycin, and clindamycin.

* * * * *

UNITED STATES PATENT AND TRADEMARK OFFICE
CERTIFICATE OF CORRECTION

PATENT NO.    : 6,432,935 B1
DATED         : August 13, 2002
INVENTOR(S)   : Marton Milankovits It is certified that error appears in the above-identified patent and that said Letters Patent is hereby corrected as shown below:

<u>Title page,</u>
Item [*], Notice, please correct to say the patent term is extended by 155 days.

<u>Column 4,</u>
Line 57, "6.5" should read -- 0.5 --

Signed and Sealed this

Fifth Day of November, 2002

Attest:

JAMES E. ROGAN
*Attesting Officer*     *Director of the United States Patent and Trademark Office*